United States Patent
Schmidt

(10) Patent No.: US 9,909,108 B2
(45) Date of Patent: Mar. 6, 2018

(54) PREPARATIONS AND METHODS FOR TREATING MALIGNANCIES

(71) Applicant: ASK Diagnostics, Inc., Norwell, MA (US)

(72) Inventor: Geoffrey Schmidt, Norwell, MA (US)

(73) Assignee: ASK DIAGNOSTICS, INC., Norwell, MA (US)

( * ) Notice: Subject to any disclaimer, the term of this patent is extended or adjusted under 35 U.S.C. 154(b) by 0 days.

(21) Appl. No.: 14/883,133

(22) Filed: Oct. 14, 2015

(65) Prior Publication Data

US 2016/0032264 A1 Feb. 4, 2016

Related U.S. Application Data

(63) Continuation of application No. 14/060,260, filed on Oct. 22, 2013, now Pat. No. 9,193,800, which is a continuation-in-part of application No. 12/811,440, filed as application No. PCT/US2008/014097 on Dec. 29, 2008, now abandoned.

(60) Provisional application No. 61/018,707, filed on Jan. 3, 2008.

(51) Int. Cl.
| | | |
|---|---|---|
| C07K 9/00 | (2006.01) | |
| C12N 9/14 | (2006.01) | |
| C07K 16/40 | (2006.01) | |
| G01N 33/573 | (2006.01) | |

(52) U.S. Cl.
CPC .............. *C12N 9/14* (2013.01); *C07K 16/40* (2013.01); *G01N 33/573* (2013.01); *C07K 2317/34* (2013.01); *C12Y 306/05* (2013.01); *G01N 2333/914* (2013.01)

(58) Field of Classification Search
None
See application file for complete search history.

(56) References Cited

U.S. PATENT DOCUMENTS 9,193,800 B2 * 11/2015 Schmidt ................. C07K 16/40

* cited by examiner

*Primary Examiner* — Sheela J. Huff
(74) *Attorney, Agent, or Firm* — Burns & Levinson LLP; Bruce D. Jobse; Janine M. Susan

(57) ABSTRACT

Disclosed are therapeutic formulations comprising antibodies against the PEKRAEKIWK (SEQ ID NO:1) epitope of the monomeric isoform of A-protein and a physiologically acceptable carrier. Methods for the treatment of subjects using these therapeutic formulations are also disclosed.

4 Claims, 2 Drawing Sheets

SEQUENCE LISTING

```
<160> NUMBER OF SEQ ID NOS: 1

<210> SEQ ID NO 1
<211> LENGTH: 10
<212> TYPE: PRT
<213> ORGANISM: Homo sapiens

<400> SEQUENCE: 1

Pro Glu Lys Arg Ala Glu Lys Ile Trp Lys
1               5                   10
```

PREPARATIONS AND METHODS FOR TREATING MALIGNANCIES

CROSS-REFERENCE TO RELATED APPLICATIONS

This application is a continuation of co-pending U.S. patent application Ser. No. 14/060,260, filed Oct. 22, 2013, entitled PREPARATIONS AND METHODS FOR TREATING MALIGNANCIES, which in turn is a continuation-in-part of U.S. patent application Ser. No. 12/811,440, which is a U.S. national stage application under 35 U.S.C. 371 of PCT/US08/14097, filed Dec. 29, 2008, which in turn claims priority to and benefit of U.S. Provisional Application No. 61/018,707, filed Jan. 3, 2008, the contents of which applications are incorporated by reference herein in their entirety for all purposes.

SEQUENCE LISTING

Reference is made to the Sequence Listing, attached hereto in both paper and computer-readable format, which forms part of this disclosure.

BACKGROUND OF THE INVENTION

This invention relates to therapeutic formulations comprising antibodies specific for the monomeric (unacylated) form of A-protein, and the use of such formulations for the treatment of cancers in a mammal.

A-protein is a cellular enzyme that was first isolated from vertebrate rod photoreceptor cells by Schmidt et al., Invest. Ophthalmol. Vis. Sci., 24:244 (1983). A-protein is also known in the scientific literature by the names $G_p$, Cockcroft, Trends Biochem. Sci., 12:75-78 (1987); recoverin Dizhoor et al, J. Biol. Chem., 267:1603316036 (1992); and CAR protein, Thirkill et al., Arch. Ophthalmol., 111:974-978 (1993). A-protein has been characterized as a GTP-binding protein (g protein), Schmidt et al., Invest. Ophthalmol. Vis. Sci., 28:94 (1987), that regulates phosphinositide metabolism by activating phospholipase C, Schmidt et al. Invest Ophthalmol. Vis. Sci., 29:123 (1988).

A-protein exists in two forms; Schmidt et al., Invest. Ophthalmol. Vis. Sci., 30:172 (1989); and Dizhoor et al., J. Biol. Chem., 267:16033-16036 (1992): as an unmodified monomer of approximately 23,000 daltons which is soluble in the cytosol (hereinafter "$A_s$"), and as a cow synthetically post-translationally modified form to which a fatty acid is attached by the action of the enzyme N-myristoyl transferase (NMT; E.C.2.3.1.97) (hereinafter "$A_m$"). The modified form of A-protein tends to self-associate as stable pentameric homopolymers with an approximate molecular weight of 130,000 daltons. These homopolymers are peripherally bound to the inner aspect of the cell membrane. The post-translational modification of A-protein induces a conformational change in the protein that renders certain peptides of the protein inaccessible to antibody binding.

In its peripherally membrane-bound form, A-protein is activated by a growth-factor receptor imbedded in the plasmalemma subsequent to activation of the receptor by a growth factor. The persistent activation of this metabolic cascade mechanism results in a sustained release of calcium into the cytosol which ultimately stimulates the cell to divide. This general scheme is referred to as signal transduction (see U.S. Pat. No. 5,100,661).

In non-ocular tissues, A-protein transduces growth signals and is expressed in mitotically active cells including malignant tissues. In cancer, A-protein is over-expressed inside affected malignant cells and into the blood stream. Fragments of the protein are also displayed on the surface of malignant cells. See Thirkill et al., Invest. Ophthalmol. Vis. Sci., 33:2768-2772 (1992).

It is well known that the immune system is a very specific mechanism for the excision of neoplastic tissues. Abbas et al., Cellular and Molecular Immunology, pp. 335-352 (1991). However, the lack of immunogenicity of carcinomas, and particularly tumor cells, has presented a stumbling block to the successful reactivation of the antitumor mechanisms of the immune system.

U.S. Patent Publication No. 2007/0053893, published Mar. 8, 2007, to Schmidt, discloses a method for reducing immunological tolerance to malignancy using formulations of myristoylCoA and N-myristoyl transferase to treat carcinomas displaying A-protein.

It will be readily appreciated that there exists a need for new and improved methods for treating cancers by blocking the monomeric form of the A-protein, and thereby stimulating the immune system to recognize cancer cells as antigenic targets for T-cells, resulting in a regression of the cancer.

SUMMARY OF THE INVENTION

The present invention provides therapeutic formulations and methods for the treatment of cancer in mammals by blocking an A-protein antigen on the cell surface to permit the targeting of the cancer cells by the immune system. Also provided are formulations and methods for the treatment of cancer by using antibodies specific for peptides uniquely accessible on the unmodified, monomeric form of A-protein ($A_s$) as vectors for the specific delivery of cytotoxic agents coupled to the antibody. This peptide has been identified as PEKRAEKIWK (SEQ ID NO:1).

According to an aspect of the present invention, a therapeutic formulation is provided which comprises an antibody specific for the monomeric form of A-protein in a physiologically acceptable carrier, in a preferred embodiment, the antibody is a monoclonal antibody, an antibody fragment, or an engineered (recombinant or humanized) antibody specific for an epitope of A-protein that is available only on the monomeric, unmodified isoforms of A-protein. The antibody can also be fused with a therapeutic compound selected from the group consisting of cancer therapeutics, cytotoxic chemicals, radioisotopes, cytotoxic animal or plant products, and compounds activated by light, for additional effectiveness. In a particularly preferred embodiment, the antibody is specific for the peptide PEKRAEKIWK (SEQ ID NO:1), or fragments thereof.

In further embodiments, the formulation can be administered systemically, preferably intravenously, to a human subject. Preferably, the antibody is encapsulated in a slow controlled release vehicle, such as a stable biopolymer or a liposome.

In another aspect, the invention relates to methods for treating cancer in a mammal by administering an effective amount of a therapeutic formulation comprising an antibody specific for the peptide PEKRAEKIWK (SEQ ID NO:1), or fragments thereof, on the soluble monomeric form of A-protein ($A_s$). Preferably, the antibody is a monoclonal antibody or antibody fragment. The antibody can be optionally fused with a therapeutic compound selected from the group consisting of cancer therapeutics, cytotoxic chemicals, radioisotopes, cytotoxic animal or plant products, and compounds activated by light. In preferred embodiments, the therapeutic formulations are administered systemically, and most preferably intravenously.

BRIEF DESCRIPTION OF THE DRAWINGS

The foregoing and other advantages and features of the invention will become apparent upon reading the following detailed description with reference to the accompanying drawing in which.

DETAILED DESCRIPTION OF THE PREFERRED EMBODIMENTS

Figure 1:
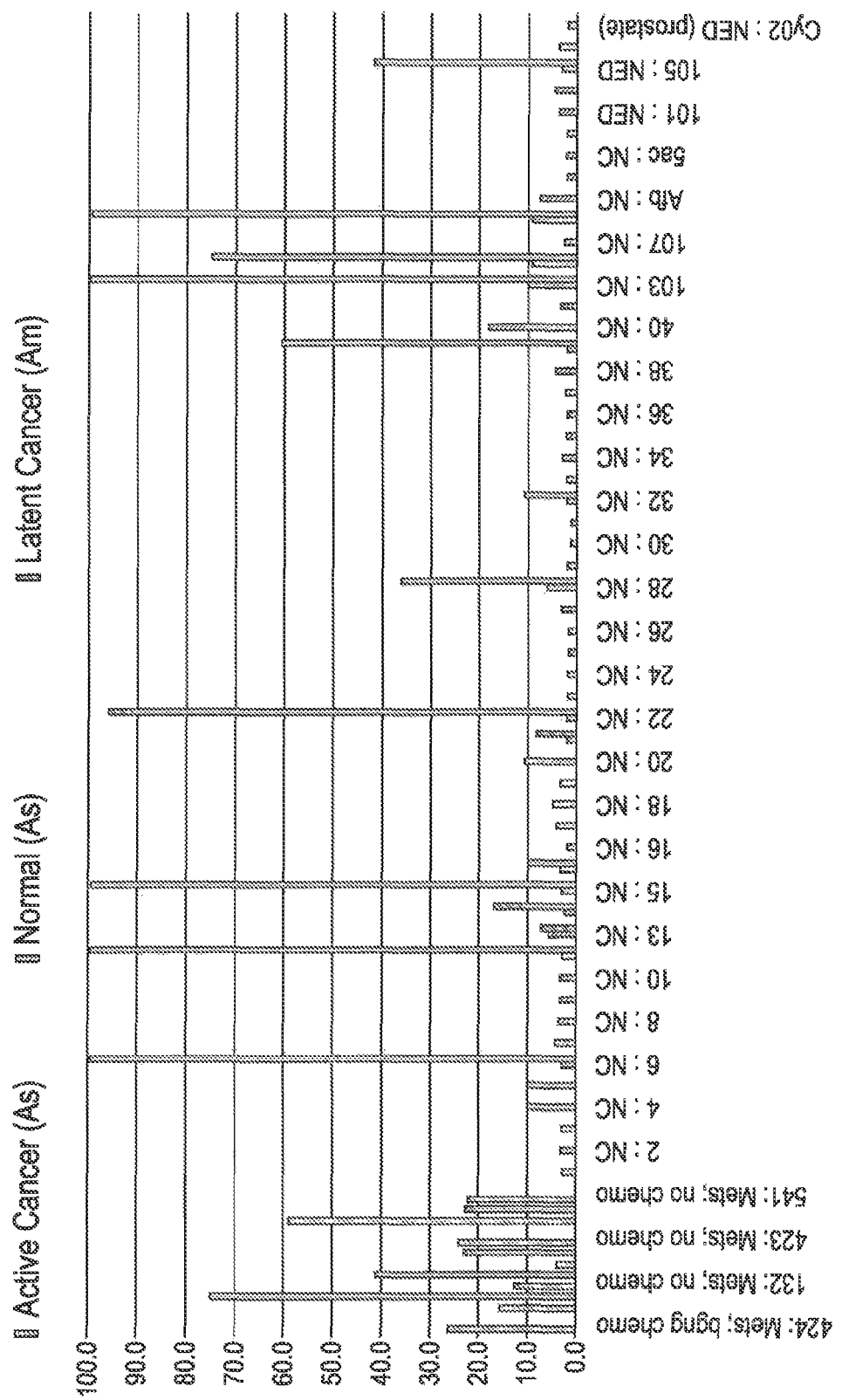
FIG. 1 is a bar graph depicting test results for breast cancer specimens for patients with latent cancer, recurrent metastatic cancer, and normal tissue specimens.

In accordance with the invention, a "therapeutically effective amount" of the therapeutic formulation is that amount of which restores the immune system's ability to recognize cancer cells as appropriate targets, or the amount necessary to deliver an effective dose of a cytotoxic agent to the cancer cells. The cancer cells are recognized as appropriate targets when antigen-specific T-cells are able to recognize as foreign those cells that had been considered native, thereby enabling an immune response to be mounted against the cells. When applied to the individual active ingredient, such as the antibody, administered alone, the term refers to that ingredient alone. When applied to a combination, the term refers to combined amounts of the active ingredients that result in the therapeutic effect, whether administered in combination, serially, or simultaneously.

The types of cancers which can be treated by the methods and formulations of this invention include any carcinomas whose primary or metastatic tumor cells produce A-protein. Such carcinomas include, but are not limited to, squamous cell, small and large cell carcinoma of the lung, and breast, colon, cervical, and prostate carcinomas. As used herein, "primary tumor" refers to tumor growth at a first site and not secondary to growth elsewhere, while "metastatic tumor" refers to tumor growth at a site other than the original growth, caused by the migration of malignant cells from the first growth.

As used herein, a "physiologically acceptable carrier" encompasses any and all solvents, dispersion media, coatings, antibacterial and antifungal agents, isotonic and absorption delaying agents and the like. The use of such media and agents for pharmaceutically active substances is well known in the art. In some embodiments, the active ingredient is embedded in a stable biopolymer for slow release. As used herein, the term "biopolymer" encompasses a biodegradable, implantable, polymeric matrix which can contain a diffusible pharmacological agent. In particular embodiments, the slow release vehicle is a liposome.

The patent and scientific literature referred to herein establishes the knowledge that is available to those with skill in the art. The issued U.S. patents, published U.S. applications, published foreign applications, and references cited herein are hereby incorporated by reference in their entirety.

It has been discovered that the modified form of A-protein causes an immune reaction while the unmodified form induces tolerance. Thus, the unmodified form of A-protein is an immunosuppressant and therefore partially or wholly responsible for the lack of immunogenicity of malignant cells.

One regulatory pathway that is absent in cancer cells is the mechanism controlling cell division which is present in mature normal cells. The lack of cellular differentiation in cancer cells may cause the partial or total loss of the ability of the cell to modify A-protein. Conversely, the lack of the substrate myristoyl, for N-myristoyl transferase in an affected cell, may result in loss of the ability to modify A-protein. Competition for myristoyl by other targets of the transferase, such as viral proteins, could result in a cellular shortage of this minor fatty acid. The change from immunoreactive, modified A-protein to immunosuppressant, unmodified A-protein correlates strongly with the earliest stages of cancer formation. This is believed to result in the overproduction of A-protein and an upset of the normal equilibrium between the monomer and the homopolymer, increasing the relative amount of monomer in the cytoplasm.

The antibody used in the formulations of the present invention binds to the PEKRAEKIWK (SEQ ID NO:1) peptide, or active fragments of this peptide. PEKRAEKIWK (SEQ ID NO:1) is an epitope unique to the monomeric form of the protein, and the formation of this antibody/antigen cell surface marker is the method by which cancer cells are identified for destruction by T-lymphocytes and macrophages in the immune system. The peptide PEKRAEKIWK (SEQ ID NO:1) epitope is accessible on the monomeric unmodified form of the A-protein ($A_s$), but not accessible on the acylated, polymeric form of the protein ($A_m$). Without wishing to be bound by any theory or mode of operation, it is believed that the conformation of the A-protein is rearranged as a result of myristoylation, making the epitope unavailable on the $A_m$ form of the protein.

In one embodiment, the therapeutic composition of the invention comprises an antibody specific for the PEKRAEKIWK (SEQ ID NO:1) epitope of the monomeric form of A-protein, in a physiologically acceptable carrier.

In other embodiments, the pharmaceutical composition may be incorporated into a slow release vehicle, such as a liposome or biopolymer. Biopolymers useful as slow release vehicles include acrylic resins, polystyrene microbeads, collagen, polyanhydrides, and other biodegradable matrices known in the art. Other slow release formulations may contain, in addition to other pharmaceutically acceptable carriers, amphipathic agents such as lipids which exist in aggregated form as micelles, insoluble monolayer, liquid crystals, or lamellar layers which are in aqueous solution. Suitable lipids for liposomal formulation include, without limitation, monoglycerides, diglycerides, sulfatides, lysolecithin, phospholipid, saponin, bile acids, and the like. The preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323.

The therapeutic compositions of the invention may contain, in addition to the active ingredient (antibody) and carrier, diluents, fillers, salts, buffers, stabilizers, solubilizers, and other materials well known in the art. The pharmaceutical composition of the invention may also contain other active factors and/or agents which stimulate an immune response to A-protein displaying cells. The pharmaceutical composition of the invention may further contain other chemotherapeutic drugs for the treatment of cancer, such as colony stimulating factors (e.g., GM-C SF).

The therapeutic compositions of the invention may be administered in accordance with the method of the invention either alone or in combination with other known therapies for cancer. When co-administered with one or more other therapies, the therapeutic of the invention may be administered either simultaneously with the other treatment(s), or sequentially. If administered sequentially, the attending physician will decide on the appropriate sequence of administering the therapeutic formulations of the invention in combination with the other therapy.

Administration of the therapeutic pharmaceutical composition can be carried out in a variety of conventional ways, such as by intraocular administration, oral ingestion, enteral administration, inhalation, or cutaneous, subcutaneous, intramuscular, or intravenous injection. Sometimes, the pharmaceutical formulation is infused into the circulatory system of the subject via injection.

When a therapeutically effective amount of the therapeutic composition of the invention is administered orally, the therapeutic composition will be in the form of a tablet, capsule, powder, solution or elixir. When administered in tablet form, the therapeutic composition of the invention may additionally contain a solid carrier such as a gelatin or an adjuvant. The tablet, capsule, or powder can contain from about 5 to 95% of the active ingredient, and preferably from about 25 to 90%. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition can contain from about 0.5 to 90% by weight of active ingredient. Sustained release oral delivery systems and/or enteric coatings for orally administered dosage forms are also contemplated such as those described in U.S. Pat. Nos. 4,704,295, 4,556,552, 4,309,404, and 4,309,406.

When a therapeutically effective amount of the therapeutic composition of the invention is administered by intravenous, cutaneous, or subcutaneous injection, the active ingredient can be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the active ingredient, an isotonic vehicle such as Sodium Chloride injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of active ingredient in the pharmaceutical composition of the present invention will depend upon the nature and severity of the condition being treated, and on the nature of prior treatments which the patient may have undergone. Ultimately, the attending physician will decide the amount of therapeutic composition with which to treat each individual patient. Initially, the attending physician may administer low doses of the therapeutic composition and observe the patient's response. Larger doses may be administered until the optimal therapeutic effect is obtained for the patient, and at that point the dosage is not increased further. The dosages are to be calculated according to the amount of A-protein in the blood of the patient, believed to vary from 5-60 ng/ml of serum, and the determined in vivo half-life of the active ingredient.

The pharmaceutical formulation can be administered in bolus, continuous, or intermittent dosages, or in a combination of continuous and intermittent dosages, as determined by the physician and the degree and/or stage of illness of the patient. The duration of intravenous therapy using the pharmaceutical composition of the present invention will vary, depending on the severity of the cancer being treated and the condition and potential idiosyncratic response of each individual patient. Ultimately the attending physician will decide on the appropriate duration of intravenous therapy using the pharmaceutical composition of the present invention.

Preferably, the pharmaceutical formulation is infused into the circulatory system of a subject afflicted with cancer. Treatment of the malignant tissue is partially or wholly accomplished by systemic treatment owing to the highly vascular nature of tumor tissue. However, in addition to systemic treatment, patients may benefit from local administration of therapeutic formulations, particularly in instances when anatomical considerations, such as enclosure of the tumor in an organ (eg. prostate, kidney, pancreas, spleen) or accessibility (eg, skin, bladder, cervix, throat) make such treatment feasible and/or desirable.

Therapeutic formulations can be contained at the site of the tumor by injection into the interstitium of an enclosed organ or anatomical space, or through surface contact with accessible tumor tissue. Surface contact can be accomplished through lavage of a hollow body space or abdomen or direct placement of the therapeutic on tissues. The active ingredient should be in an appropriately stabilized form that allows for maximum local exposure and minimum escape into other body compartments. It may be useful to utilize impregnated biopolymers for slow release of drugs. In the case of direct application, stabilizing substances such as creams, lotions, or liposomes may be useful.

The method and route of administration of the therapeutic formulation of the invention will depend, to a large extent, on the location of the affected tissue.

In the case of a malignant tumor, the tumor itself is the source of A-protein and the site of the A-protein displayed as a surface antigen. Accordingly, higher concentrations of the active ingredient in the immediate vicinity of the tumor are desirable. Local administration also lowers the systemic dosages required.

Recombinant antibodies can be produced using a phage display, for instance, which involves using a virus or yeast to create the antibodies. This involves the rapid cloning of immunoglobulin gene segments to create libraries of antibodies with slightly different amino acid sequences from which antibodies with desired specificities can be selected. Antibody production can be expanded in fermentation chambers.

The monomeric form of A-protein (the antigen for antibody production) is readily obtainable from biological sources, such as bovine retinas, as described in more detail in Schmidt et al., J. Biol Chem. 262:14333-14336 (1978).

A-protein can also be obtained by cloning a human genomic or retinal library according to the methods of Dizhoor et al., J. Biol. Chem., 267:16033-16036 (1992). Briefly, this entails constructing oligonucleotide probes that are complementary to portions of the cDNA sequence of A-protein. See, for instance, Polans et al, J. Biol. Chem., 112:981-989 (1991). The library is expanded by polymerase chain reaction and expressed in a host vector such as *E. coli* which has the human DNA subcloned into its chromosomes.

Bacteria are grown in culture dishes and the plaques are screened with the positive plaques are selected and rescreened two more times. The gene product of selected plaques is checked for the correct sequence, corresponding to that of A-protein.

A-protein can also be cloned from a human genomic or retinal library according to the method of Ray et al., Proc. Natl. Acad. Sci. 89:5705-5709 (1992). Briefly, this entails constructing oligonucleotide probes that are complementary to portions of the cDNA sequence of A-protein. The library is expanded by polymerase chain reaction and expressed in a host vector such as E. coli which has the human DNA subcloned into its chromosomes. Bacteria are grown in culture dishes and the plaques are screened with the oligonucleotide probes. Positive plaques are selected and rescreened at least twice. The gene product of selected plaques is checked for the correct sequence, corresponding to that of A-protein.

The antibodies of the invention can advantageously be fused with therapeutic compounds and molecules for improved efficacy. Suitable compounds and molecules for fusion include, but are not limited to, cancer therapeutics, cytotoxic chemicals and molecules, radioisotopes, cytoxic animal or plant derivatives, and compounds activated by light.

The following example is intended to illustrate one aspect of the invention without limiting it thereby.

EXAMPLES

A study was conducted to determine the feasibility of using the methods of the present invention in a clinical environment. The study was conducted on a variety of tissue and blood samples for different cancer types versus normal tissue and blood samples. The tests were performed using a sandwich. ELISA format utilizing proprietary monoclonal antibodies for the latent disease assay. The test for active cancer utilized one monoclonal and one rabbit polyclonal antibody in the sandwich format.

Antibodies against the $A_s$ isotype of A-protein were used in a single blind study of patients with recurrent metastatic breast cancer against normal controls. Normal specimens were mixed with breast cancer patient specimens and blinded. Additional control specimens including normals and patients in remission (NED=no evidence of disease), were supplied. All specimens were tested in triplicate, and the results were returned to investigators prior to breaking the code.

Referring to FIG. 1, the values for the latent cancer test are considered significant if over 20 pig/ml. Values for patients with a positive diagnosis for recurrent metastatic cancer are considered positive if over 10 µg/ml. Normal #40 as shown in FIG. 1 is considered to be positive for an undiagnosed cancer.

FIG. 1 demonstrates that $A_s$ and $A_m$ are successfully discriminated from each other by the specificity of the antibodies used. The lack of "multispecificity" is seen in specimens that contain either one or both of the isotypes of A-protein, such as specimens that contain only $A_s$ and have no $A_m$ signal, and conversely, specimens that contain $A_m$ but show no $A_s$ signal.

The experiment above was repeated and expanded in a second trial that used the test for $A_s$ to assay a pool of normal and cancer patient specimens. In this trial, a number of different cancers were tested against normals with antibodies specific for the PEKRAEKIWK (SEQ ID NO:1) peptide. The results of this study are depicted in FIG. 2.

Figure 2:
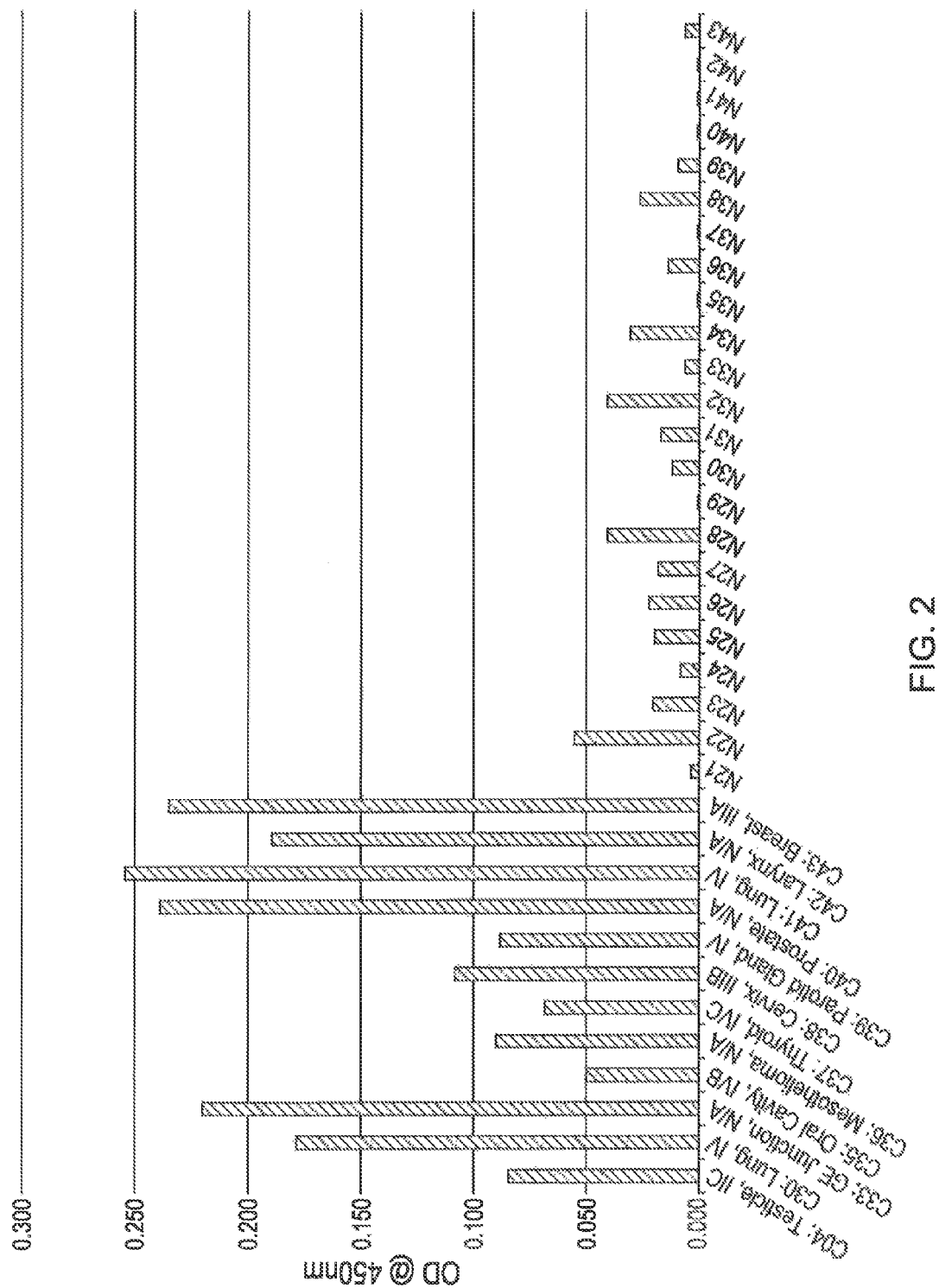
FIG. 2 is a bar graph depicting test results for patient specimens with different cancer types using antibodies specific, for the PEKRAEKIWK (SEQ ID NO:1) peptide.

The study for FIG. 2 was performed on a variety of cancers versus normals. Specimens were obtained from a commercial biorepository. All specimens were tested in triplicate. The tests were performed using a sandwich ELISA assay format utilizing a proprietary rabbit polyclonal antibody, and a commercial antibody specific for A-protein, the target protein. Values are represented as OD units.

Summarizing the above studies, the results demonstrate that assays specific for the $A_s$ form of A-protein, utilizing antibodies made against the PEKRAEKIWK (SEQ ID NO:1) peptide, recognize $A_s$ in a variety of cancers without cross-recognition of $A_m$ which is found in both the cancer and normal populations.

Those skilled in the art will recognize, or be able to ascertain, using no more than routine experimentation, numerous equivalents to the specific substances and procedures described herein. Such equivalents are considered to be within the scope of this invention, and are covered by the following claims.

---

---

What is claimed is:

1. A composition comprising peptide PEKRAEKIWK (SEQ ID NO: 1) and a pharmaceutically acceptable carrier, wherein the carrier comprises a gelatin or an adjuvant.

2. The composition of claim 1, wherein said composition is a means of producing an antibody capable of discriminating between soluble A-protein ($A_s$) and modified A-protein ($A_m$).

3. The composition of claim 2, wherein said antibody comprises a monoclonal antibody, an antibody fragment, a recombinant antibody or a humanized antibody.

4. The composition of claim 3, wherein said antibody is fused to a therapeutic compound comprising cancer therapeutics, cytotoxic chemicals, radioisotopes, cytotoxic animal products, cytotoxic plant products or compounds activated by light.

* * * * *